US 6,609,016 B1

(12) United States Patent
Lynn

(10) Patent No.: US 6,609,016 B1
(45) Date of Patent: Aug. 19, 2003

(54) MEDICAL MICROPROCESSOR SYSTEM AND METHOD FOR PROVIDING A VENTILATION INDEXED OXIMETRY VALUE

(76) Inventor: Lawrence A. Lynn, 1275 Kinnear Rd., Columbus, OH (US) 43212

(*) Notice: Subject to any disclaimer, the term of this patent is extended or adjusted under 35 U.S.C. 154(b) by 330 days.

(21) Appl. No.: 09/628,655

(22) Filed: Jul. 28, 2000

Related U.S. Application Data

(60) Continuation-in-part of application No. 09/409,204, filed on Sep. 30, 1999, now Pat. No. 6,342,039, which is a division of application No. 09/115,226, filed on Jul. 14, 1998, now Pat. No. 6,223,064.
(60) Provisional application No. 60/201,735, filed on May 4, 2000, provisional application No. 60/146,146, filed on Jul. 30, 1999, provisional application No. 60/052,438, filed on Jul. 14, 1997, and provisional application No. 60/052,439, filed on Jul. 14, 1997.

(51) Int. Cl.[7] .................................................. A61B 5/00
(52) U.S. Cl. ........................ 600/323; 600/324; 600/529
(58) Field of Search .................................. 600/309–310, 600/322–324, 300, 484, 529, 533

(56) References Cited

U.S. PATENT DOCUMENTS

| | | | | |
|---|---|---|---|---|
| 4,106,503 A | * | 8/1978 | Rosenthal et al. | 128/200.18 |
| 4,651,746 A | * | 3/1987 | Wall | 600/483 |
| 5,318,597 A | | 6/1994 | Hauck et al. | |
| 5,353,788 A | * | 10/1994 | Miles | 128/204.23 |
| 5,743,250 A | * | 4/1998 | Gonda et al. | 128/200.14 |
| 5,765,563 A | | 6/1998 | Vander Schaaf | |
| 5,803,066 A | | 9/1998 | Rapoport et al. | |
| 5,827,179 A | | 10/1998 | Lichter et al. | |
| 6,083,156 A | * | 7/2000 | Lisiecki | 600/301 |
| 6,120,441 A | * | 9/2000 | Griebel | 600/300 |
| 6,148,814 A | | 11/2000 | Clemmer et al. | |
| 6,223,064 B1 | * | 4/2001 | Lynn et al. | 600/324 |
| 6,342,039 B1 | | 1/2002 | Lynn et al. | |
| 6,463,326 B1 | | 10/2002 | Hartley et al. | |

* cited by examiner

*Primary Examiner*—Eric F. Winakur
*Assistant Examiner*—Matthew Kremer
(74) *Attorney, Agent, or Firm*—Nixon & Vanderhye P.C.

(57) ABSTRACT

Pathologic relationship trending of an oxygen saturation time series relative to a corresponding ventilation time series is identified used a medical microprocessor system, and an increasing difference between the two time series is detected and displayed. That increasing difference is provided for evaluating a patient and for detecting early evidence of serious illness. A patient's normal predicted time ventilation may also be calculated using one or more of the patient's height, weight, sex, and body surface area. A relationship is determined between measured blood oxygen saturation, measured time ventilation, and predicted time ventilation. The microprocessor preferably determines the presence of an interval of steady state ventilation and measures the timed ventilation during that interval. The microprocessor also measures the oxygen saturation corresponding to that determined, steady state ventilation interval. The microprocessor then calculates a Ventilation Oximetry Index (VOI) of minute ventilation and oxygen saturation as measured by pulse oximetry. The VOI assists the medical clinician in judging the potential effect of the measured minute ventilation on the oxygen saturation value and in identifying when additional testing (such as an arterial blood gas) is indicated.

37 Claims, 3 Drawing Sheets

MEDICAL MICROPROCESSOR SYSTEM AND METHOD FOR PROVIDING A VENTILATION INDEXED OXIMETRY VALUE

This application is related to U.S. patent application Ser. No. 09/115,226 (the disclosure of which is incorporated by reference as if completely disclosed herein).

RELATED APPLICATIONS

This application claims priority from provisional application Ser. No. 60/146,146, filed Jul. 30, 1999 and Ser. No. 60/201,735, filed May 4, 2000, the disclosures of which are incorporated herein by reference. This application is a continuation-in-part of U.S. patent application Ser. No. 09/409,204, filed Sep. 30, 1999, now U.S. Pat. No. 6,342,039, which is a divisional of U.S. patent application Ser. No. 09/115,226, filed on Jul. 14, 1998, now U.S. Pat. No. 6,223,064, (both applications claiming priority from U.S. provisional application serial Nos. 60/052,438, filed Jul. 14, 1997 and 60/052,439, filed Jul. 14, 1997).

BACKGROUND AND SUMMARY OF THE INVENTION

This invention relates to methods and devices for use in clinical medicine particularly to provide the integration of the measurement of oxygen saturation of arterial blood and the associated minute ventilation from which the oxygen saturation is derived to enhance the clinical utility of the oxygen saturation measurement.

The brief measurement of oxygen saturation by pulse oximetry in the assessment of shortness of breath is a standard medical practice. This is commonly known as "spot (oximetry," as is differentiated from continuous oximetry monitoring in that the oxygen saturation measurement is made for a brief period of time (such as 30 seconds to 5 minutes) and then generally reported as a single value (such as the average oxygen saturation or lowest oxygen saturation). There has been a trend toward smaller, more compact oximeters, which do not record or print out the saturation values but rather provide a digital reading of the number (such as "96%"). Unfortunately, this trend toward using a single spot "number," while more simple and convenient, does not take into account the dynamic interrelated mechanisms operative to generate the oximetry number.

Spot oximetry provides important information, is useful as a screening test, and is often employed as an additional "routine $5^{th}$ vital sign" along with temperature, pulse, respiration, and blood pressure. Unfortunately, spot oximetry measurement has serious limitations which are often not considered by physicians and respiratory therapist is ordering them. To understand the clinical significance of these limitations and their potential to adversely affect patient care, it is important to understand how spot oximetry is used in clinical medicine on the hospital wards.

Spot oximetry provides important information, is useful as a screening test, and is often employed as an additional "routine $5^{th}$ vital sign" along with temperature, pulse, respiration, and blood pressure. Unfortunately spot oximetry measurement has serious limitations which are often not consider by the physicians and respiratory therapist ordering them. To understand the clinical significance of these limitations and their potential to adversely affect patient care, it is important to understand how spot oximetry is used in clinical medicine on the hospital wards.

Commonly, indeed thousands of times each day, a respiratory therapist, intern, resident or other physician is called to see a hospitalized patient for the evaluation shortness of breath. Often the first diagnostic test ordered is a spot oximetry test. Many medical personnel think of this measurement as pivotal. The thinking goes like this, "if the spot oximetry measurement is within the normal range then the shortness of breath is much less likely to reflect a problem which is life threatening." This is a common misconception and leads to the general and widespread use of spot oximetry on hospital wards as a test to assess the immediate clinical significance of shortness of breath. Unfortunately, as will be discussed, spot oximetry is a poor indicator of the immediate clinical significance of shortness of breath and a normal spot oximetry value commonly provides the health care worker with a false sense of security which can lead to a poor patient outcome due to delayed diagnosis.

The present inventor has long attempted to instruct interns and medical residents of the hazards of using spot oximetry in this way. But teaching alone cannot correct this ubiquitous problem. Even within the hospital of the present inventor, each year the stability of the respiratory state of many patients is misconstrued by interns and respiratory therapists by the false sense of security provided by a normal spot oximetry value, and timely patient treatment is delayed. Given the frequency of this problem within a hospital wherein active teaching of the hazards of spot oximetry is provided, it is likely that nationwide, thousands of patients have delayed intervention every year due to the improper interpretation of the significance of a normal spot oximetry measurement.

When considering the management of critically ill patients, the timing of intervention is of paramount importance. The value of any diagnostic test is in part determined by the ability of the test to predict adverse physiologic events early in the course of the disease process wherein intervention is more likely to be effective. This is particularly true of the diseases associated with infections such as toxic shock, sepsis, and pneumonia or with thromboembolic disease. Regrettably, with respect to early identification of impending respiratory failure or severe respiratory dysfunction, spot oximetry is very poor.

The lack of utility of spot oximetry as an early indicator of impending respiratory failure has as it's physiologic basis the position the overall significance arterial oxygen saturation has to human cellular respiration and survival. The arterial saturation, as determined by the spot oximetry test, is one of the most important parameters defining the sufficiency of lung function and oxygen delivery to the tissues. This is one of the reasons that physicians give a normal reading such significance, but it is also the reason that the human body protects oxygen delivery by keeping the value of arterial oxygen saturation close to the normal value till death is very near. In humans, a primary protective mechanism is immediately operative to keep the arterial oxygen saturation value high until late in the course of critical illness such that the patient will increase the volume of air breathed per minute which will "blow off carbondioxide" and which will raise the oxygen saturation. (With a normal respiratory quotient the partial pressure of oxygen increases by 1.2 mm for each 1 mm the CO2 falls, while the associated rise in oxygen saturation in response to a fall in CO2 is dependent on the position of the oxygen saturation on the oxyhemoglobin dissociation curve). This often occurs early in the course of the illness (such as sepsis) before any fall in oxygen saturation has occurred and can be seen as a "preventive" survival mechanism protecting the patient against a fall in oxygen saturation before it occurs. The fall in CO2 caused by the increased minute ventilation also increases the affinity of hemoglobin for oxygen, this means that at any given level of partial pressure of oxygen, the arterial oxygen saturation as measured by a spot oximetry device is higher. In other words, despite a decline in the lung's ability to keep the dissolved arterial oxygen in the normal range the spot oximetry reading can still be entirely normal due to this compensatory mechanism.

A final confounding factor is anxiety. Anxiety causes an increase in minute ventilation, which raises the spot oximetry value due to the mechanisms noted supra. Unfortunately, in some patients, the increased minute ventilation can be associated to a greater extent with larger volume breaths than with a marked increase in respiratory rate. For this reason, increased minute ventilation may be subtle and not recognized during clinical assessment. The classic case is the anxious young woman with a vaginal discharge. The spot oximetry value may be normal even as she is dying of toxic shock. Her body is protecting the oxygen delivery to the tissues and the anxiety is driving the CO2 lower further increasing the spot oximetry value. But the intern, or emergency room physician, may misconstrue the anxiety and the increased minute ventilation and fail to recognize the impact it has on the spot oximetry value. The physician seeing a perfect spot oximetry value of 97% for example may feel reassured that the patient is not in danger of respiratory failure during the night. However, with toxic shock there is no time to lose. When the compensating mechanisms are exhausted, such patients deteriorate rapidly, often over 6–12 hours, too rapidly for the physician seeing the patient the next day to intervene.

In addition to the problems noted above there is another mechanism by which the common application of spot oximetry is adversely affecting timely medical intervention. From a more scientifically enlightened perspective the spot oximetry can be seen as a simple test which can actually only provide information about the arterial oxygen saturation and pulse. When applied in this limited manner, the test is both sensitive and specific for a fall in arterial oxygen saturation, which is indeed an important abnormality to identify. However, this is not the way the test is used clinically. The test is commonly used as an initial screen, as an initial substitute for an arterial blood gas in the evaluation of shortness of breath. Indeed a very common mistake is to start with a spot oximetry test and if that is normal to dispense with the blood gas test, which is more painful, time consuming and costly. This is due to the fact that many health care workers do not recognize that spot oximetry is an insensitive test when applied to determine the presence of even severe respiratory or metabolic dysfunction. When used in this way the test is being applied in a much larger manner than the role for which it is suited i.e. it is being used, as a preliminary substitute for an arterial blood gas to initially assess the respiratory status of the patient generally. Spot oximetry cannot provide that function. In fact when used in that manner the spot oximetry test has the potential to cause significant harm as a function of delayed diagnosis, by providing a false impression that an arterial blood gas is not necessary. A patient with metabolic acidosis, for instance, due to late sepsis, will often have superimposed respiratory alkalosis and a normal spot oximetry study. The spot oximetry study, when used to determine the need for an arterial blood gas will, in this case, commonly be normal until very late (too late). If a spot oximetry test is used as an initial screen, the blood gas may not be obtained and the diagnosis of this volatile and potentially fatal critical condition may be seriously delayed.

Education is not the solution; the hazards of the spot oximetry test are too abstract for many physicians and therapists. Many do not fully understand the complex interactions of the dynamical physiologic systems defining an evolving critical illness. Also many healthcare workers have not had sufficient training in the physiology of critical illness to fully grasp the limited relevance of isolated "spot" measurements of instantaneous parameters at any given point along the time continuum. In addition the dynamical interactions of multiple compensatory mechanisms are pivotal and in aggregate these issues are simply too complex for many non-physiologist clinicians. Yet every physician and respiratory therapist in the hospital is expected to understand a spot oximetry test as if it were as simple as a temperature measurement.

The present inventor became frustrated with the difficulty associated with attempts to mitigate this problem through education of interns and residents, and in discussing the problem with other pulmonary specialists, he found the problem to be ubiquitous. To solve this problem the present inventor designed a simple portable medical device which provides enhanced information relating to magnitude of operative compensatory mechanisms relating to the gas exchange status of the patient and therefore is superior to the measurement of spot oximetry for the assessment of shortness of breath on hospital wards. The device further provides a mechanism to identify those patients wherein the spot measurement is likely to spuriously suggest normality. And further it is a portable, hand-held device, which can rival spot oximetry in its simplicity. For these reasons, it provides an improved initial screening test for shortness of breath in that, like an arterial blood gas, it is a more sensitive indicator of the presence of evolving respiratory instability than the spot oximetry but, like spot oximetry, it is both simple and inexpensive to apply. Further the testing is non-invasive and does not cause pain. Perhaps most importantly, the device generates "a simple number", "a parameter" which combines the value of the oximetry reading and the magnitude of compensatory or confounding mechanisms. This can aid in simplifying the assessment process and reduce the potential for errors. Since the "number" generated includes automatic adjustments for compensation, the physician or therapist is provided with a more accurate picture of the status of the respiratory system. The pragmatics, the "real world" of this issue cannot be overstated. It is critical that any device competing with spot oximetry for a place as an initial screening test of shortness of breath be very simple, inexpensive, noninvasive, portable, compact, and it must generate a simple "number" or index which the physician or therapist can use along with clinical assessment to decide whether the pain, and expense of an arterial blood gas measurement is indicated. It is the purpose of the present invention to provide all of these features as well as other features as will be evident from the discussion which follows.

The present invention uses a comparison of the minute ventilation with the oximetry measurement to determine indexed oxygen saturation. As discussed supra, in health, the oxygen saturation is increased by a rise in minute ventilation as a function of the effect such rise has to increase alveolar oxygen partial pressure and to reduce carbondioxide levels. Since all patients have deadspace ventilation, and since the dead space ventilation is variable from patient to patient and even within the same patient with different tidal breaths, it is not possible to reliably determine the true alveolar pCO2 (or alveolar O2) by measuring the minute ventilation alone.

However precise determination of these numbers is not necessary. Indeed the spot oximetry value itself is not a precise measurement of the arterial oxygen saturation of hemoglobin but is rather an approximation. It can therefore be seen that both spot oximetry and the ventilation indexed oximetry test of the instant invention are general parameters intended to be applied along with clinical assessment to determine the need for the more precise testing associated with arterial blood gas measurement.

Generally one presently preferred embodiment of the present invention is a ventilation indexing oximeter including a ventilation measurement device for generating a first result indicative of the volume of gas ventilated by a patient per unit of time, an oximeter for generating a second result indicative of the oxygen saturation of human blood corresponding to the first result, and a microprocessor programmed for comparing said first result with said second result to generate a third result indicative of both said first result and said second result.

The ventilation-measuring device preferably comprises a flow sensor capable of determining the minute ventilation of a patient. The first result, which can be the average minute ventilation, can be determined for a first time interval. The second result, which can be the average oxygen saturation of arterial blood as determined by pulse oximetry, can be determined for a second time interval which can commence after or near the end of the first time interval. The first time interval is sufficient for said patient's respiratory status to become stabilized. The second time interval can be shorter than said first time interval. The third result can be a calculated index of said first result and said second result.

In one preferred embodiment, the present invention provides a microprocessor system generating a mathematical comparison of concomitantly or near concomitantly measured oxygen saturation and timed ventilation gas measurement. In the preferred embodiment, a mathematical comparison is provided of the average arterial pulse oximetry measurement and the associated measured average minute ventilation (timed ventilated volume) of all ventilated gasses within a given measurement interval. One preferred embodiment provides a microprocessor to calculate the index as the measured minute ventilation divided by the predicted resting normal minute ventilation for the patient's age, body surface area, and sex (as is well known in the art). The Oximetry measurement is indexed to adjust for the potential effect of increased minute ventilation to increase the saturation.

It is the purpose of the present invention to provide a microprocessor system, which compares the measured arterial saturation to the timed ventilation from which it was derived.

It is further the purpose of the present invention to provide an index, which improves the clinical utility of the measured pulse oximetry value.

It is further the purpose of the present invention to provide a portable, handheld ventilation indexing oximeter to measure and display the arterial oxygen saturation and to indicate the corresponding minute ventilation from which it was derived provide an improved, immediate clinical assessment of shortness of breath at the bedside.

It is further the purpose of the present invention to provide a continues moving mathematical comparison of the arterial oxygen saturation and the corresponding ventilated gas measurement from which it was derived so that the magnitude of change in ventilated gas measurement required to induce a given magnitude of change in arterial saturation can be optimally assessed.

DESCRIPTION OF THE PRESENTLY PREFERRED EMBODIMENT

Figure 1:
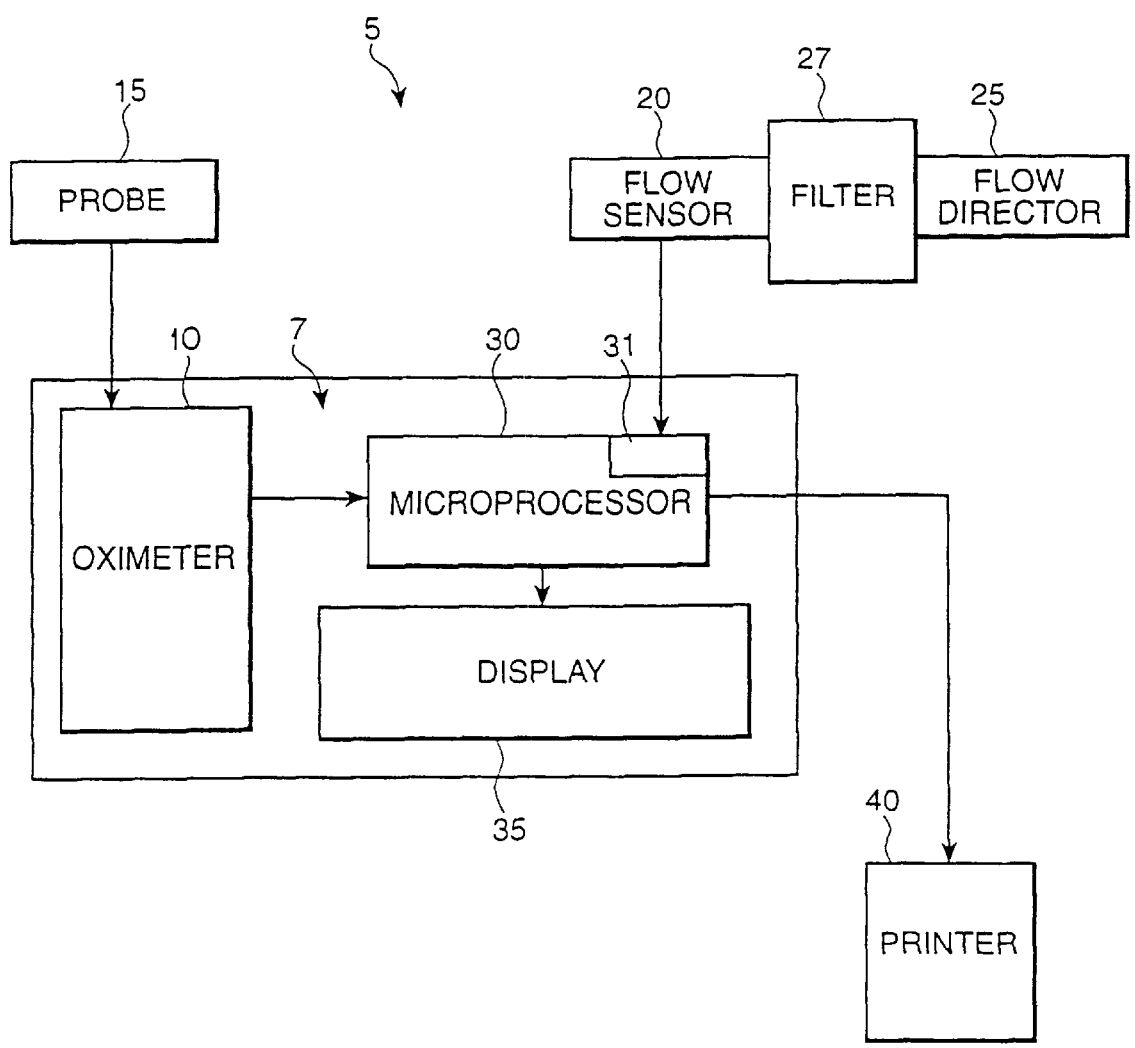
FIG. 1 is a schematic view of one preferred embodiment of the ventilation indexing pulse oximeter according to the present invention.

As shown in FIG. 1, a single compact flow indexing oximeter 5 includes a housing 7 of a size and configuration such that it can easily be hand held and carried directly to the patient's bedside. The housing 7 includes a pulse oximeter 10 connectable with an external probe 15 for interfacing with a body part of the patient. The oximeter 10 is preferably a pulse oximeter capable of continuous measurement with a high sampling frequency (such as one hertz or greater), (such oximeters are well known in the art). Either a transillumination or a reflectance pulse oximeter may be used. The flow indexing oximeter 5 further includes a flow sensor 20, which is preferably a pneumotachometer connectable with a flow director 25. The flow director 25 is sized and configured for placement adjacent the mouth and/or nose. A disposable filter 27 can be provided intermediate the sensor 20 and flow director 25. The flow director 25 is preferably a disposable plastic tube sized to be a sealing fit between the patient lips and includes an integral filter 27 (as is used with conventional spirometer. Alternatively, a mask for covering at least a portion of the mouth and/or nose can be used. Alternatively the flow director 25 can be defined by a low pressure region positioned adjacent one side of the face such as can be provided by a vacuum hose or tube connected to an orifice of a face mask The flow sensor 20 can be of the type generating an analog signal as is well known in the art, such as a pneumotachometer, or the minute ventilation can be determined by volume measurement as is provided by rotating seal spirometer or by other methods. The minute ventilation can be measured on inhalation or exhalation but flow is preferably measured on both inhalation and exhalation so that the cumulative mean or mid flow rates and mean durations of all inhalations can be compared to the mean duration of all exhalations within the measured time interval if desired. A microprocessor 30 is provided for processing and calculating the oxygen saturation as is known in the art and having an input receiver 31 for connection with flow sensor 20. The processor further has a data input interface 33 (such as a keypad) for inputting the patient's height, weight, sex, age, and race (if desired). The processor is programmed to automatically calculate the predicted normal value for resting minute ventilation based on the input values (as is known in the art). The microprocessor 30 is programmed to apply the process algorithm shown in FIG. 2 and then generate an output on display window 35, which can be a continuous graphical output. In addition, if preferred the output can be sent to a printer 40. The flow indexing oximeter 5 is preferably an integral device including both the oximeter 10, the microprocessor 30 and the input for the flow sensor in the same compact housing or otherwise as a compact connectable unit. It is preferable that the flow sensor 20 be separate from the flow indexing oximeter 5 so that the device 5 need not be held near the patient's face.

Figure 2:
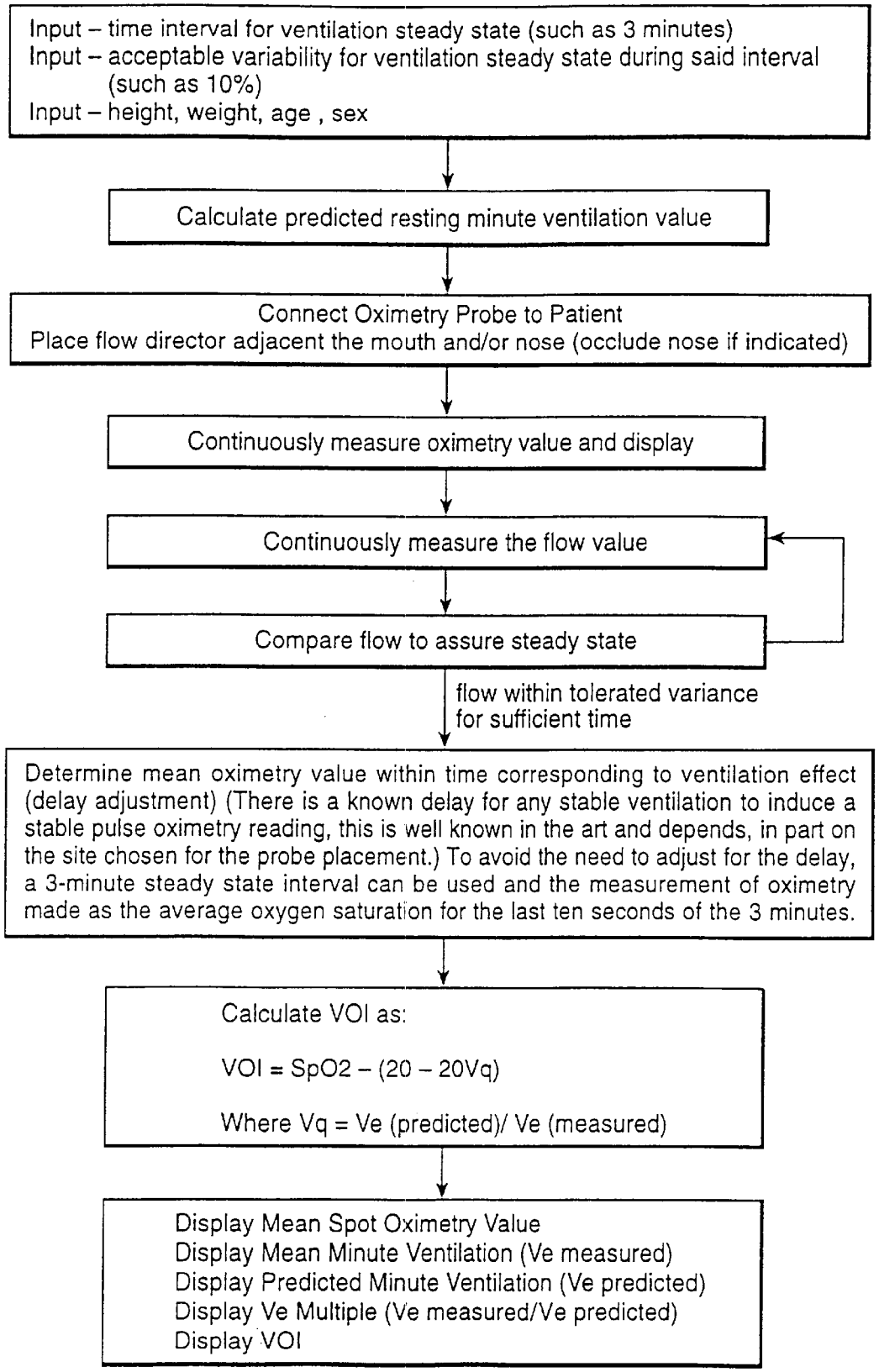
FIG. 2 is a block diagram of the processes of a ventilation indexing oximeter according to the present invention
Figure 3:
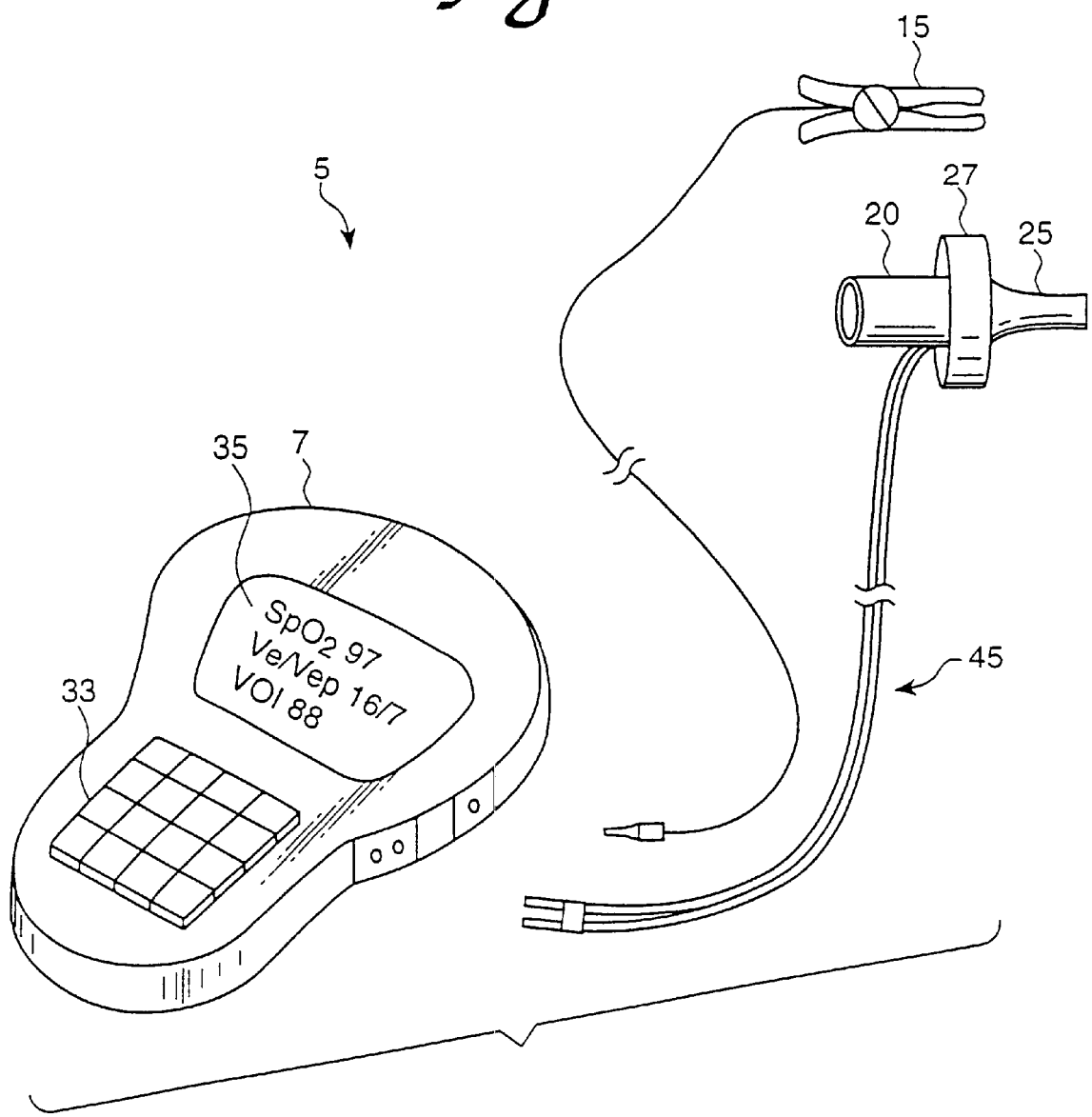
FIG. 3 is a perspective view of one presently preferred embodiment of the invention showing the input for the oximeter probe and the tubing connections of the pneumotachometer on the same side.

As shown in FIG. 2, the microprocessor 30 is programmed to calculate a value, which the present inventor calls the "Ventilation Oximretry Index" (VOI). The VOI is not measured value but rather a calculated index of minute ventilation and oxygen saturation as measured by pulse oximetry. This value is used to provide a simple reference number to assist the clinician in judging the potential effect of the measured minute ventilation on the saturation value (i.e., "What might the oxygen saturation be if the patient was ventilating a normal volume of air.") and to help identify when additional testing such as an arterial blood gas is indicated. Potential factors influencing increasing the difference between the measured oximetry value and the VOI include:

Compensatory Hyperventilation in response to hypoxemia.

Metabolic acidosis

Hyperventilation of critical illness.

Hyperventilation due to anxiety or pain.

Increased deadspace ventilation.

Hypermetabolic state

It should be noted that the VOI could be higher than the measured saturation in the presence of hyperventilation.

The microprocessor 30 includes a display and/or printer, which outputs the average oxygen saturation (SpO2), the average minute ventilation (Ve), and the VOI. In operation the physician orders a ventilation indexed oximetry measurement. The therapist carries the compact handheld device to the patient's bedside and places the gas flow director 25 adjacent the face. The therapist applies the probe 15 adjacent a portion of the patient's body and instructs the patient to rest and breath normally. The flow sensor 20 monitors flow until a steady state (such as plus or minus 10% flow) is reached for a predetermined time (preferably at least 90 seconds although a longer time for example 3–5 minutes may be used if desired), the average oximetry derived saturation corresponding to the arterial oxygen saturation derived from that minute ventilation time interval is measured. This can be performed by measuring the average saturation during the last 10 seconds at the end of a 3 minute steady state interval since this would be sufficient time for both steady state and the transmission time delay to have been achieved. (In another preferred embodiment the average saturation is determined for a 10-second interval after the anticipated delay after the steady state interval wherein said anticipated delay is adjusted for the site of probe placement and pulse.) The measured and calculated values are then displayed. The values are used in combination with clinical assessment to determine the need for additional testing such as arterial blood gas measurement.

The purpose of the index is to estimate the SaO2 (saturation of arterial blood) value which could be present in the patient under test if the patient did not have active compensatory or pathophysiologic mechanisms operative. The calculated VOI therefore provides an index relating to the reliability of the SpO2 value as an indicator of respiratory stability. The higher the SpO2 (measured saturation of arterial blood by pulse oximetry) to VOI difference, the less reliable the SpO2 value is as an indication of respiratory stability and the more critical it is for the physician to consider additional diagnostic evaluation, monitoring, and/or testing. It can be seen that the VOI is an estimated value of the effect of a change in ventilation on SpO2 given normal physiologic mechanisms. For this reason, the calculation VOI value need not be over embellished mathematically, and it is not the purpose of the index to precisely calculate a physiologic parameter but rather provide a useful index to be used in conjunction with a more precisely measured parameter to help guide the process of bedside clinical decision making.

More specifically the presently preferred formula (as formula 1 in FIG. 2) is derived as an estimate of the potential effect on the measured SpO2 value induced by the difference between the Ve (measured minute ventilation) and the (Vep) predicted normal resting minute ventilation The following formula estimates the predicted change in paCO2 (dCO2) induced by a given measured minute ventilation wherein the normal value for paCO2 is 40:

$$dCO2=40-40(Vep)/Ve)$$

By linearization of the oxyhemoglobin disassociation curve over the range from 80% saturation to 100% saturation and the assumption that the respiratory quotient is normal (0.8) the potential effect a given reduction in pCO2 could have to change the SO2 (dSO2) as a function of the attendant change in partial pressure of oxygen is estimated as:

$$dSO2=0.5(dCO2)$$

and finally the VOI is calculated as:

$$VOI=SpO2-dSO2$$

Beyond the pragmatics of real world physician assessment, it is important from a purely mathematical perspective not to render complex the calculation of a clinically calculated index. The application of complex formulas to measured parameters derived within the limitations of precision associated with conventional bedside clinical measurements and relating to dynamical biologic systems is mathematically naive. The clinical assessment of the physiologic state of a critically ill patient is not a precise matter since sufficient information concerning many interrelated operative physiologic systems in any given patient care situation are always unknown and cannot be reasonably assumed with any degree of precision. Complex mathematical calculations are misleading in that, by their complexity they imply precision. In fact the present inventor and others have shown that when applied to clinically derived data such as arterial blood gas measurements, such complex calculations lead to error propagation and magnification which render the output imprecise in any regard. See *Effect of measurement error on calculated variables of oxygen transport*, by Woda R, Dzwoncznk R, Orlowski J, Van Lente F, and Lynn L, *Journal of Applied Physiology*, 80(2): 559–563, 1996.

For these reasons, the above more simplified calculation is presently preferred, however, a more comprehensive formula could be derived adjusting the change in SpO2 induced by a given estimated change in paO2 using the Severinghaus equation as is known in the art. Furthermore, if the carbondioxide production is known, as can be obtained using the present invention by the addition of a main stream or side stream pCO2 monitor as is known in the art, then the PaCO2 can be estimated using the known formula:

$$PaCO2=0.863(VCO2)/(Ve-Vpds)$$

Where Vds is equal to the normal predicted deadspace ventilation per minute.

Based upon this teaching, it will be clear to those skilled in the art that additional microprocessor derived indexes using a mathematical or graphical comparison of minute ventilation and SpO2 may be derived to enhance the clinical utility of a measured SpO2 value.

Using formula 1 the VOI is intended to provide a value approximating the effect on PCO2 which is induced in association with an increase in minute ventilation that would be expected with a normal deadspace. Since disease states are associated with increased deadspace they have a tendency to reduce the potential effect of any given increase in minute ventilation to increase the oxygen saturation. Yet the presence of an increased deadspace itself is relevant to the clinical need for additional testing such as is provided by an arterial blood gas. This is particularly true if the presence of a high deadspace is unanticipated clinically (as is often the case with pulmonary embolism). It can be seen that the potential effect that an increase in minute ventilation associated with a rise in deadspace will have to reduce the VOI is not a disadvantage since the low VOI will provide a warning that an arterial blood gas is indicated for such patients. One issue is the presence of Chronic Obstructive Lung Disease or Asthma. These patients have a high deadspace and will be expected to have a low baseline VOI due to the increased minute ventilation needed to compensate for this. In these patients a low VOI is anticipated and this provides a warning of the increased potential hazard associated with limiting the study of such a patient's gas exchange parameters to noninvasive evaluation such as a spot oximetry test. Also in such patients the identification a falling VOI is particularly useful.

It can be seen that the VOI is most useful in the assessment of shortness of breath in patients without obstructive lung disease but that the test still has clinical utility in that population especially if a very low value is identified or if the value is falling with serial measurements. One alternative approach in the evaluation of shortness of breath is to go directly to the arterial blood gas measurement without preliminary noninvasive testing. This is the preferred alternative to spot oximetry in the evaluation of a person short of breath (such as for example a postoperative patient) without evidence of active obstructive disease, since the oximetry reading is more likely to provide a false sense of security than to provide any useful information (since an arterial blood gas is indicated in any regard). This approach has been advised in lectures by the present inventor for years but is rarely implemented perhaps because doctors and therapists find the simplicity and ease of the spot oximetry measurement too enticing to pass up. Regrettably, having applied the test many cannot seem recognize that they should not be reassured by the finding of a normal value. Therein lies considerable danger.

Whereas the spot oximetry value provides no useful information which cannot be better derived from an arterial blood gas, the VOI actually provides information not available on the arterial blood gas in that it is an index based on the relationship between a measured averaged minute ventilation during a time interval and arterial oxygen saturation derived from said interval of said measured average ventilation. No such indexed relationship can be determined from the arterial blood gas measurement alone. For all these reasons, the determination of the VOI is a better first test than spot oximetry.

The invention is used in the following way to change the approach clinically to the initial evaluation of shortness of breath. To understand and contrast the significance of this invention it is important first to consider the pragmatic, real world approach often taken by physicians in the complex and inexact environment in which they work where the choice of testing is determined by many interacting factors.

The following is an illustrative clinical case, which demonstrates of the potential pitfalls of the present common practice of using spot oximetry as an initial screening test.

Consider a 40 year old male who has just had a simple laparoscopic gallbladder resection 1 day earlier. He develops pain in the right lower chest and the intern is asked to see the patient. The intern notices that the patient also has tenderness in the right upper quadrant and believes the chest pain is referred from the abdomen due to his surgery. But the intern also notes he is slightly short of breath, which the intern thinks is due to postoperative pain and anxiety. Just to be sure, the intern then orders a spot oximetry test to evaluate the mild shortness of breath, wishing to avoid for the patient the pain of an arterial blood gas test. The respiratory therapist carries the oximeter to the patient's bedside and places the probe on the patient's finger. The oximeter displays a saturation of 97% saturation (perfectly normal). The intern is reassured and goes to see the next patient. That night the patient dies of pulmonary embolism.

Obviously an arterial blood gas was the right test to perform but this did not occur for several reasons. Here are some of the reasons this hypothetical patient was not diagnosed in life:

1. The chest pain was mild and explainable in the basis of referred pain from the abdomen.
2. The shortness of breath was mild and thought to be due to anxiety.
3. The intern wished to minimize the patient's discomfort by ordering a non-invasive spot oximetry test first to see if additional testing was necessary.
4. The intern's planned specialty was general surgery and she has not yet had sufficient training in the clinical relevance of complex respiratory physiologic interactions as they relate to the spot oximetry measurement on the hospital wards.

The point is the above illustrative case is to show that in the real world the issues defining the choice of initial testing are very subtle and complex and that an improved initial noninvasive testing method is required to prevent the delayed identification of patients at risk for impending respiratory failure.

Now consider the same case with the present invention. The intern is called, and instead of a spot oximetry test, she orders a ventilation indexed oximetry test. The respiratory therapist carries the hand-held ventilation indexing oximeter to the patients bedside, inputs the patients weight, height, sex, and age. Then while the patient is sitting at rest, places the probe on the patients finger and the flow tube in the patient's mouth and occludes the nose, the flow indexing oximeter monitors the flow and determines when steady state has been achieved within the pre-selected range and for the pre-selected time. The oxygen saturation occurring within or subsequent to that time (adjusting for the delay of pulse oximetry response as is known in the art) is measured.

The ventilation indexing oximeter displays an oximetry reading of 97%, (exactly the same "reassuring, perfect" number read by the spot oximeter), but in addition the ventilation indexing oximeter shows a minute ventilation of 2 times the predicted value, and a ventilation oximetry index of 87. The intern, impressed by unexpectedly the low VOI and orders a blood gas, which reveals a PO2 of 75 and a PCO2 of 28. The intern sees the severe A-a gradient and transfers the patient to ICU, obtains a pulmonary consult, starts heparin, orders a VQ scan and the patient goes home in a few days.

This illustrates the value of ventilation indexing the VOI to provide a better alternative first test then conventional spot oximetry. The use of the present invention can shift the initial evaluation to a new alternative simple noninvasive screening method, which evaluates both oxygen saturation, the magnitude of compensatory or confounding mechanisms operative to sustain that oxygen saturation, and the potential relationship of the oxygen saturation to those compensatory or confounding mechanisms.

There are other way that oximetry can be indexed for ventilation. Alternately, the minute ventilation of a single exhaled gas such as carbon dioxide can be used and this will provide a measure of the carbon dioxide production as well as the average end tidal pCO2 which can be used as additional parameters to determine the significance of any given spot oximetry value. In one preferred embodiment the microprocessor is programmed (as is known in the art) to function also as a conventional spirometer. This allows the flow indexing oximeter to also function as a full featured spirometer so that the respiratory therapist, after obtaining, the flow indexed oximetry reading can perform a forced vital capacity maneuver to asses airway function. As discussed, obstructive pulmonary disease affects the dead space, and therefore potentially influences the VOI value. The addition of conventional spirometry functions to allow the ventilation indexing oximeter to provide a measurement of peak flow, force expiratory volume in one second, and forced vital capacity along with the minute ventilation and flow indexed oximetry value from one inexpensive handheld, compact device. This can provide a very efficient and innovative new multitasking device for the respiratory therapist, which can further enhance the marketing value of the flow indexing oximeter of the present invention.

Although a simple tube based flow director is preferred because of its low cost and ease of use, when long, term measurement of ventilation indexed oximetry, as during sleep is desired the flow sensor 20 and /or the oximeter probe 15 may be mounted with the oximeter 10 and flow director 25 in the same compact housing 7 for attachment with the patient (such as for example can be achieved by mounting a battery powered flow indexing reflectance oximeter of the present invention on a face, or nasal mask so that only the application of a single mask over the face is required.). Alternatively, the flow indexing oximeter may be mounted to the mask and can include an ear pulse oximeter probe so that a finger connection is not required such that the entire device is mounted with the patient's head.

When ventilation indexed oximetry is measured with the present invention during, a overnight study, it is preferably performed with a plot of the VOI as a function of time in a graphical format along with other timed waveforms such as the oximetry tracing, minute ventilation tracing, and if desired EEG and other typical sleep parameters as part of a sleep montage. The addition of the graphical plot of the VOI adds the ability to easily identify a disparate relationship between minute ventilation and oxygen saturation such as is typical of patients with primary pulmonary disease. The oximeter to VOI difference widens in such patients markedly when auto peep develops as a function of hyperventilation as during the recovery phase from sleep apnea. For the graphical tracing, the delay for each probe system (such as with a finger probe) is provided in the input so that the for VOI calculation is made based on a moving window of the average ventilation over a pre-selected preceding interval (such as 1 minute) immediately prior to the anticipated delay interval. The basis (steady state or non-steady state) of the VOI signal can be designated, for example, when the flow signal has been within the preset steady state range for the preset duration the graphical waveform of the VOI can be colored green and when the VOI is generated by a non-steady state reading the color can be red.

For sleep studies, the VOI as described above is only calculated for oximetry saturations greater then 80% and when the minute ventilation falls to zero the calculation, as described supra is, of course, is not made. The plotted continues measurement of overnight minute ventilation and the plotted continues calculation of the VOI in sleep apnea will provide a clustering of waveform cycles as described in the previously referenced patent application and can be analyzed using the object oriented method discussed in that application to enhance both the diagnostic evaluation of sleep apnea, determine its severity, and to assist in identifing co-morbidities such as sustained hyperventilation, or primary pulmonary disease. Without the continuous calculation of the VOI, a continuous microprocessor based comparison of the oximetry saturation and the minute ventilation is still made comparing, in one preferred a magnitude of change in minute ventilation to a magnitude of corresponding change in oxygen saturation. In one embodiment a moving window averages the measured saturation over a time period (such as 10 seconds) and compares this a corresponding moving window averaging minute ventilation over a time period (such as 10 seconds) continuos plot of a comparison index (such as the indexes noted supra can be generated from this continues calculation. Also the mean change in saturation (dSpO2) corresponding to a the mean change in minute ventilation (dVe) can be reported, as for example (dSpO2/dVe), comparing 10 or 20 second epochs for example or for specific periods (such as REM periods) or for the entire night as a for example quotient of these respective values. The dSpO2/dVe is an indicator of the presence of pulmonary disease with higher values for any given value of SpO2 occurring during health. The dSpO2/dVe can be indexed for the absolute value of SpO2 since there will be less increase in SpO2 for any given increase in minute ventilation with higher SpO2 values due to the sigmoid shape of the oxyhemoglobin dissociation curve. This quotient can be reported along with the mean absolute values.

In one preferred embodiment using a microprocessor to integrate and compare the minute ventilation signal and the oximetry signal during a sleep study, the microprocessor is programmed to identify the onset and magnitude of apneas or hypopneas and compare the delay between the fall or cessation in minute ventilation and the resultant fall in oxygen saturation (after adjusting for the expected delay). Patients with a rapid and early fall (e.g. less than 20 seconds) have low oxygen stores. If such patients have been hypoventilating (as for at least 30 seconds prior to the apnea onset) or there is a short duration between apnea (e.g. less than 15 seconds) this would explain the low stores. However, if such patients have been hyperventilating prior to the apnea and the interval prior to the next apnea is long such as greater than 30 seconds than an early and rapid fall is suggestive of associated cardiovascular or pulmonary disease. The integration of minute ventilation with oximetry on a continuos basis during sleep can be used by the sleep physician to suggest the presence co-morbidities which may warrant further investigation or which may indicate that the use of auto-cpap titration may be sub-optimal (as with severe sustained hypoventilation or when the VOI is persistently quite low.)

It will be evident to those skilled in the art that, based on this teaching of methods and devices to integrate and compare, using a microprocessor, the output of an oximeter and minute ventilation measuring device that there are many ways to provide the numerical or graphical ventilation indexed oximetry measurements and comparisons of the present invention both for sleep diagnosis and on the hospital wards.

Although the presently preferred embodiments of this invention have been described, it will be obvious to those skilled in the art that various changes and modifications may be made without departing from the spirit and scope of the invention.

What is claimed is:

1. A microprocessor system for an evaluation of a patient, the system comprising a processor programmed to:
   (a) receive a first input indicative of said patient's measured timed ventilation;
   (b) receive a second input indicate of said patient's measured arterial oxygen saturation, said saturation corresponding to said timed ventilation;
   (c) receive a third input of at least one of said patient's height, weight, sex, and body surface area;
   (d) calculate said patient's normal predicted timed ventilation based at least on said third input; and
   (e) determine a relationship between at least said measured arterial saturation, said measured timed ventilation and said predicted timed ventilation.

2. A system as in claim 1 wherein said relationship is an index of said measured oxygen saturation relative to a mathematical comparison of said measured ventilation and said predicted ventilation.

3. A system as in claim 1 wherein said relationship is a calculated index derived from at least said first, second and third inputs.

4. A system as in claim 1 wherein said processor is sized to be handheld.

5. A system as in claim 4 wherein said system further includes a handheld display, said processor being programmed to output at least said relationship to said handheld display.

6. A system as in claim 5 wherein said processor is further programmed to output said first input and said second input to said handheld display.

7. A system as in claim 3 wherein said system further includes a ventilation measurement device for measuring said first input.

8. A system as in claim 2 wherein said ventilation measurement device is a pneumotachometer.

9. A system as in claim 2 wherein said system further includes an oxygen saturation measurement device for measuring said second input.

10. A system as in claim 9 wherein said system is sized to be handheld.

11. A system as in claim 10 wherein said system further includes a display, said system being programmed to output at least said relationship to said display.

12. A system as in claim 11 wherein said processor is further programmed, to output said first input and said second input to said display.

13. A system as in claim 2 wherein said ventilation measurement device is a spirometer.

14. A system as in claim 3 wherein said system further includes an oxygen saturation measurement device for measuring said second input.

15. A system as in claim 14 wherein said oxygen saturation measurement device is a pulse oximeter.

16. A patient monitor for evaluating a patient, the monitor having a display, the monitor comprising:
   (a) a device for measuring ventilation capable of producing a first output of timed ventilation;
   (b) a pulse oximeter capable of producing a second output indicative of said patient's arterial oxygen saturation;
   (c) an input device capable of receiving an input of at least one of a patient's body dimensions; and
   (d) a processor programmed to:
      (d1) determine the presence of an interval of steady state ventilation and the timed ventilation during said interval to generate a first output,
      (d2) measure oxygen saturation corresponding to said interval to generate a second output,
      (d3) calculate said patient's predicted ventilation based on at least one of said body dimensions, and
      (d4) display at least said first output, said second output, and said predicted ventilation.

17. A patient monitor as in claim 16 further including a housing for containing at least said processor, said housing being sized to be easily held in a human hand.

18. A patient monitor as in claim 12 wherein said housing is attached with said oximeter.

19. A patient monitor as in claim 18 wherein said housing further contains at least a portion of said device for measuring ventilation.

20. A patient monitor as in claim 12 wherein said housing contains at least a portion of said oximeter.

21. A patient monitor as in claim 12 wherein said housing is attached with said device for measuring ventilation.

22. A patient monitor as in claim 21 wherein said ventilation measurement device is configured for communication with an airflow receiver for receiving the flow of gas from at least one of a patient's mouth and nose, said monitor including a communication port for communicating with at least one of said ventilation measurement device and said airflow receiver.

23. A patient monitor as in claim 21 wherein said device for measuring ventilation is a pneumotachometer.

24. A patient monitor as in claim 12 wherein said oximeter is configured for communication with a probe for mounting with a patient's body part, said monitor including a communication port for communicating with said probe.

25. A patient monitor as in claim 16 wherein said processor is further programmed to:
   (d5) compare said first output and said predicted timed ventilation to render a third output, and
   (d6) display said third output.

26. A patient monitor as in claim 16 wherein said processor is further programmed to:
   (d5) compare said first output, said predicted ventilation, and said second output to render a fourth output,
   (d6) display said fourth output.

27. A patient monitor as in claim 16 wherein said first output is the average minute ventilation during said interval of steady state ventilation.

28. A patient monitor as in claim 16 wherein said processor is further programmed to identify a second time interval for measuring said oxygen saturation, said second time interval corresponding with said time interval of steady state ventilation.

29. A patient monitor as in claim 28 wherein said second output is the average arterial oxygen saturation measured during said second time interval, said first time interval and said second time interval corresponding such that said second output is the average oxygen saturation generated by the gas exchange of the patient during said interval of steady state ventilation.

30. A patient monitor as in claim 29 wherein said time interval of steady state ventilation defines a first onset and said time interval for measuring said oxygen saturation defines a second onset, said first onset occurring before said second onset.

31. A microprocessor system for evaluating a patient and for detecting early evidence of serious illness in said patient by the identification of pathologic relational trending of an oxygen saturation time series relative to a corresponding ventilation time series, the system comprising a processor programmed to:

(a) receive a first input of a time series of measured ventilation values to derive a first output indicative of a first trend of timed ventilation, (b) receive a second input of time series of measured arterial oxygen saturation to derive an output indicative of a second trend of oxygen saturation, said first time series corresponding to said second time series, (c) compare said first trend and said second trend to identify a increasing difference between said first trend and said second trend; and (d) output an indication of said increasing difference.

32. A system as in claim 31 wherein said comparing comprises calculating a relationship between said first input and said second input to derive a calculated index.

33. A system as in claim 32 wherein said processor is further programmed to derive a third trend of said index.

34. A patient monitor for evaluating a patient, the monitor having a display, the monitor comprising:

(a) a device for measuring ventilation capable of producing a first output of timed ventilation;

(b) a pulse oximeter capable of producing a second output indicative of said patient's arterial oxygen saturation;

(c) an input device capable of receiving an input of at least one of a patient's body dimensions; and (d) a processor programmed to:

(d1) determine the presence of an interval of steady state ventilation and the timed ventilation during said interval to generate a first output, (d2) measure oxygen saturation corresponding to said interval to generate a second output, and (d3) display at least said first output and said second output.

35. A patient monitor as in claim 34 wherein said processor is further programmed to calculate an index of said first and second outputs.

36. A patient monitor as in claim 34 wherein said timed ventilation is a volume of gas ventilated per unit time.

37. A patient monitor as in claim 34 wherein said timed ventilation is a total volume of room air ventilated per unit time.

* * * * *